(12) United States Patent
Gilson et al.

(10) Patent No.: US 7,922,741 B2
(45) Date of Patent: Apr. 12, 2011

(54) SUPPORT FRAME FOR AN EMBOLIC PROTECTION DEVICE

(75) Inventors: Paul Gilson, Moycullen (IE); Michael Gilvarry, Ballina (IE); Eamon Brady, Elphin (IE); David Vale, Dublin (IE); Steven Horan, Athlone (IE)

(73) Assignee: Salviac Limited, Dublin (IE)

( * ) Notice: Subject to any disclaimer, the term of this patent is extended or adjusted under 35 U.S.C. 154(b) by 750 days.

(21) Appl. No.: 11/762,148

(22) Filed: Jun. 13, 2007

(65) Prior Publication Data

US 2007/0233177 A1    Oct. 4, 2007

Related U.S. Application Data

(63) Continuation of application No. 11/505,469, filed on Aug. 17, 2006, which is a continuation of application No. 10/797,612, filed on Mar. 11, 2004, now abandoned, which is a continuation of application No. 09/986,132, filed on Nov. 7, 2001, now abandoned, which is a continuation of application No. PCT/IE00/00054, filed on May 8, 2000.

(30) Foreign Application Priority Data

May 7, 1999    (WO) .................. PCT/IE99/00035

(51) Int. Cl.
*A61M 29/00* (2006.01)
(52) U.S. Cl. ....................................................... 606/200
(58) Field of Classification Search .................. 606/113, 606/114, 127, 159, 200
See application file for complete search history.

(56) References Cited

U.S. PATENT DOCUMENTS 4,790,812 A * 12/1988 Hawkins et al. .............. 606/159
(Continued)

FOREIGN PATENT DOCUMENTS

EP        461375        12/1991
(Continued)

*Primary Examiner* — Kevin T Truong
(74) *Attorney, Agent, or Firm* — Sughrue Mion, PLLC; Jonathan Feuchtwang

(57) ABSTRACT

An embolic protection device comprises a collapsible filter element for delivery through a vascular system of a patient. The filter element comprising a collapsible filter body and a filter support frame contacting the filter body. The collapsible filter body has an inlet end and an outlet end, the inlet end of the filter body having one or more inlet openings sized to allow blood and embolic material to enter the filter body, the outlet end of the filter body having a plurality of outlet openings sized to allow through passage of blood but to retain undesired embolic material within the filter body. The filter support frame is movable between a collapsed position for movement through the vascular system and an extended outwardly projecting position to support the filter body in the expanded position. The frame has a plurality of engagement segments which are spaced-apart longitudinally and transversely when the filter body is in the deployed expanded configuration to urge the filter body into opposition with the vessel wall. The engagement segments define at least partially a substantially helical engagement track.

20 Claims, 17 Drawing Sheets

U.S. PATENT DOCUMENTS

| | | | |
|---|---|---|---|
| 5,254,662 A | 10/1993 | Szycher et al. | |
| 5,621,065 A | 4/1997 | Pudleiner et al. | |
| 5,954,745 A * | 9/1999 | Gertler et al. | 606/200 |
| 6,059,814 A * | 5/2000 | Ladd | 606/200 |
| 6,152,946 A * | 11/2000 | Broome et al. | 606/200 |
| 6,179,859 B1 * | 1/2001 | Bates et al. | 606/200 |
| 6,277,138 B1 | 8/2001 | Levinson et al. | |
| 6,336,934 B1 * | 1/2002 | Gilson et al. | 606/200 |
| 6,346,116 B1 * | 2/2002 | Brooks et al. | 606/200 |
| 6,391,044 B1 | 5/2002 | Yadav et al. | |
| 6,530,939 B1 * | 3/2003 | Hopkins et al. | 606/200 |

FOREIGN PATENT DOCUMENTS

| | | |
|---|---|---|
| WO | WO 98/39053 | 9/1998 |
| WO | WO 99/16382 | 4/1999 |
| WO | WO 99/23976 | 5/1999 |
| WO | WO 99/24084 | 5/1999 |

* cited by examiner

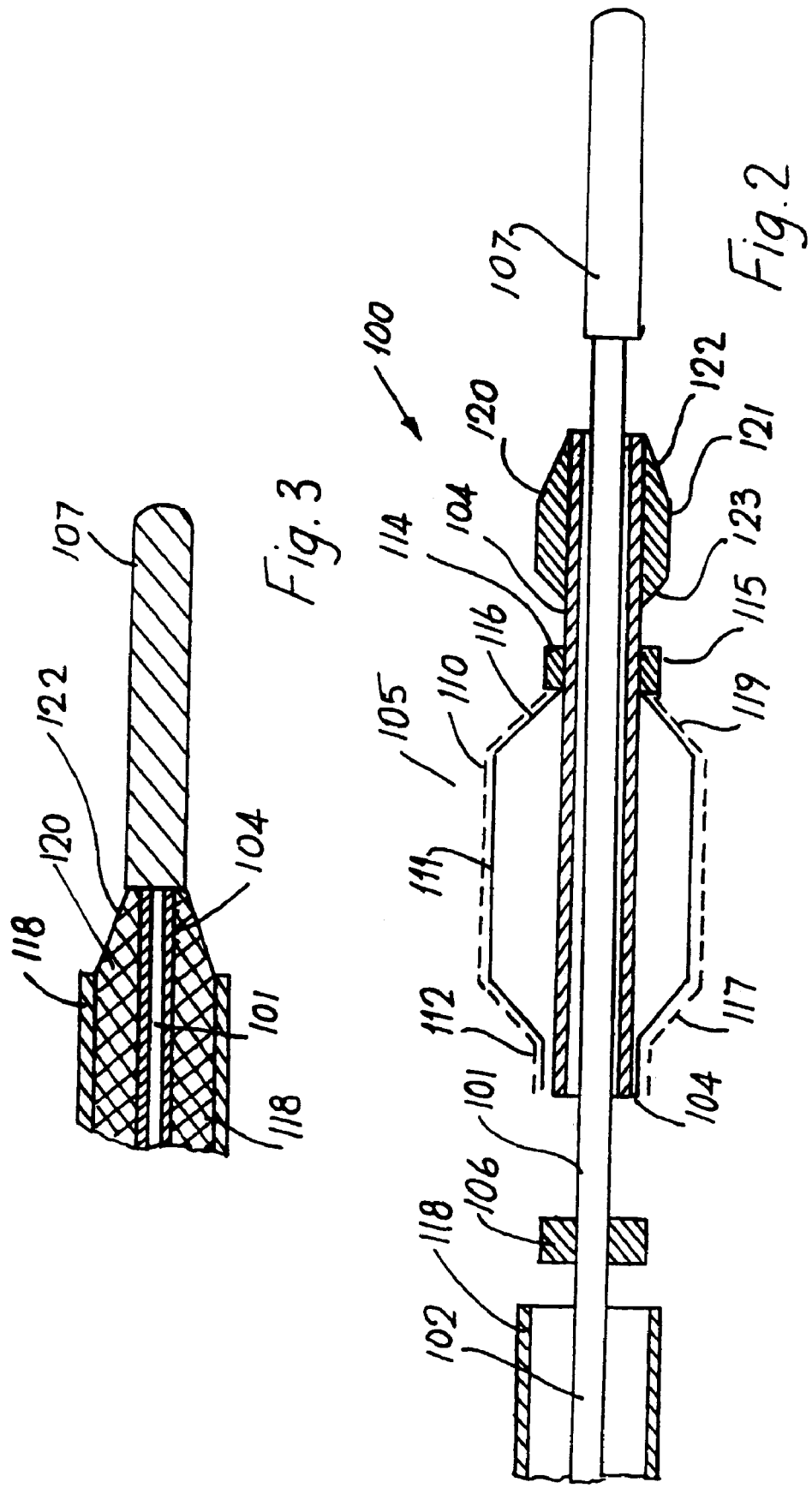

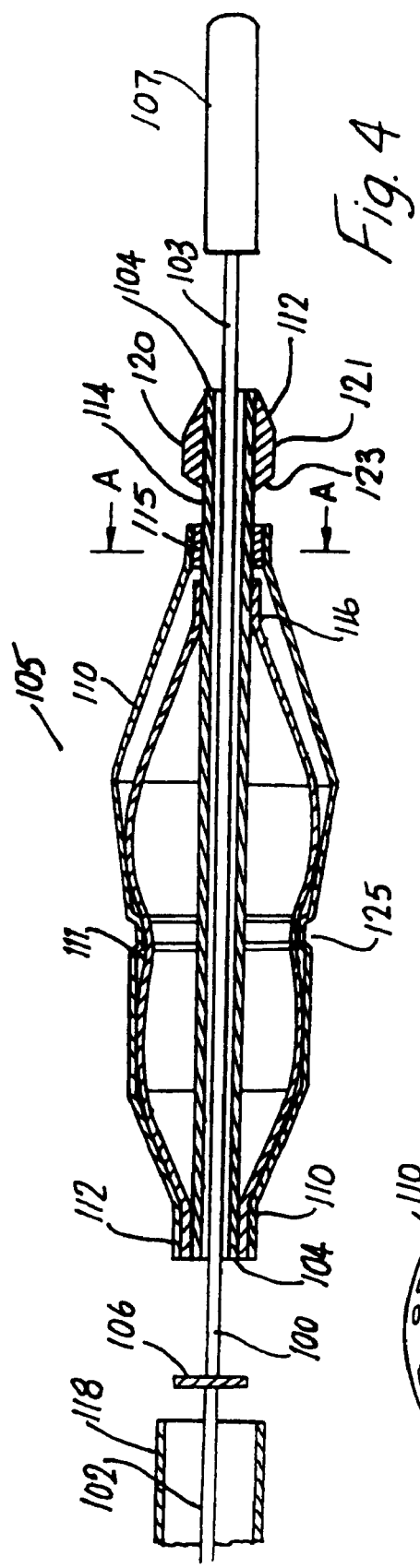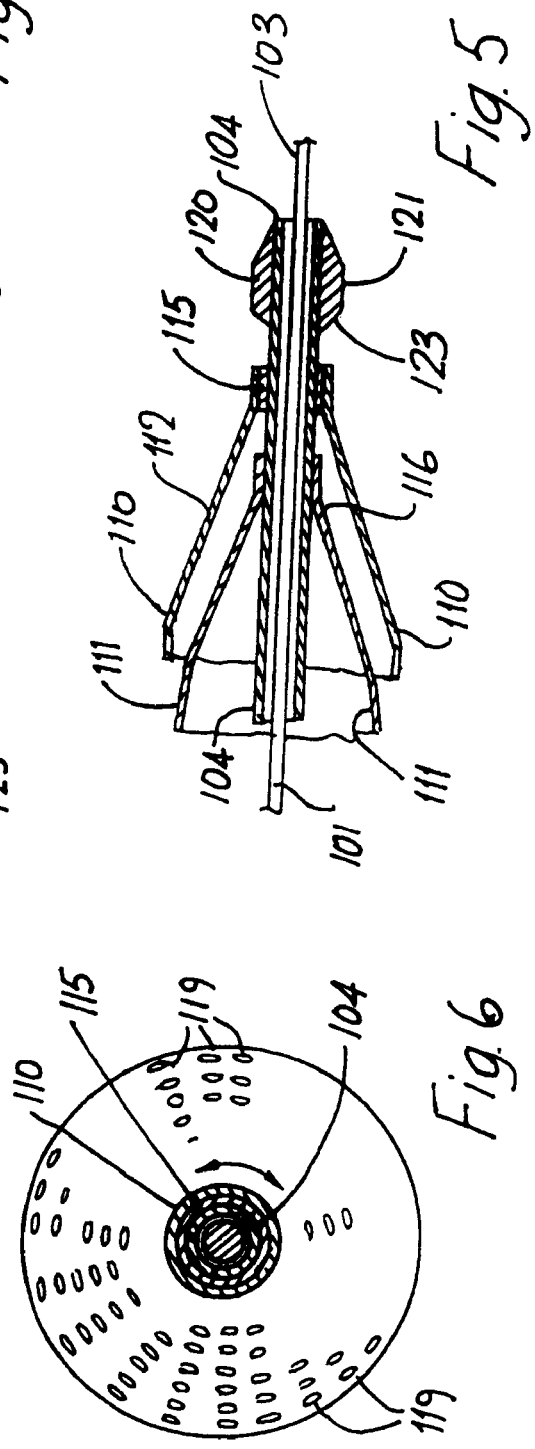

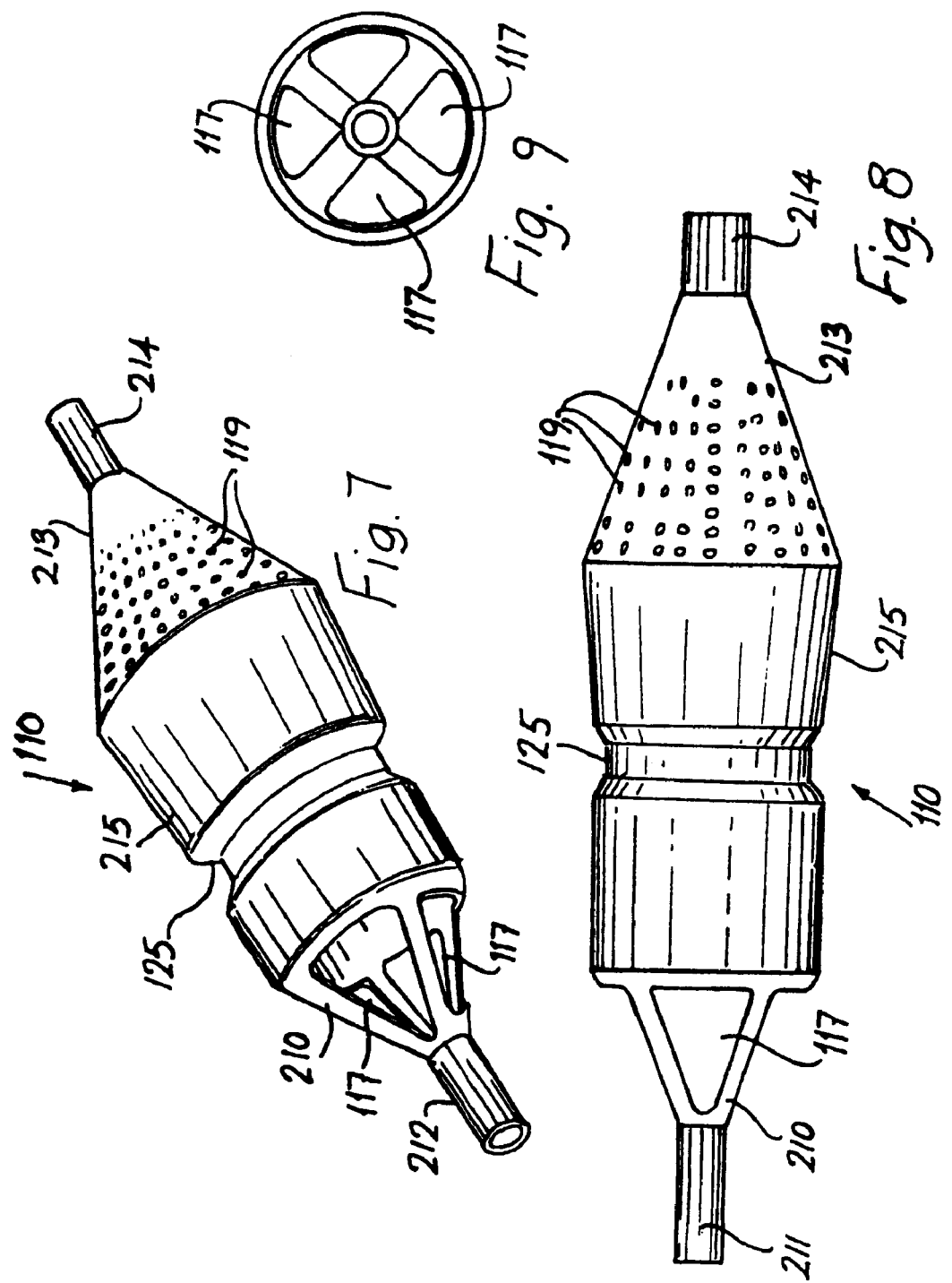

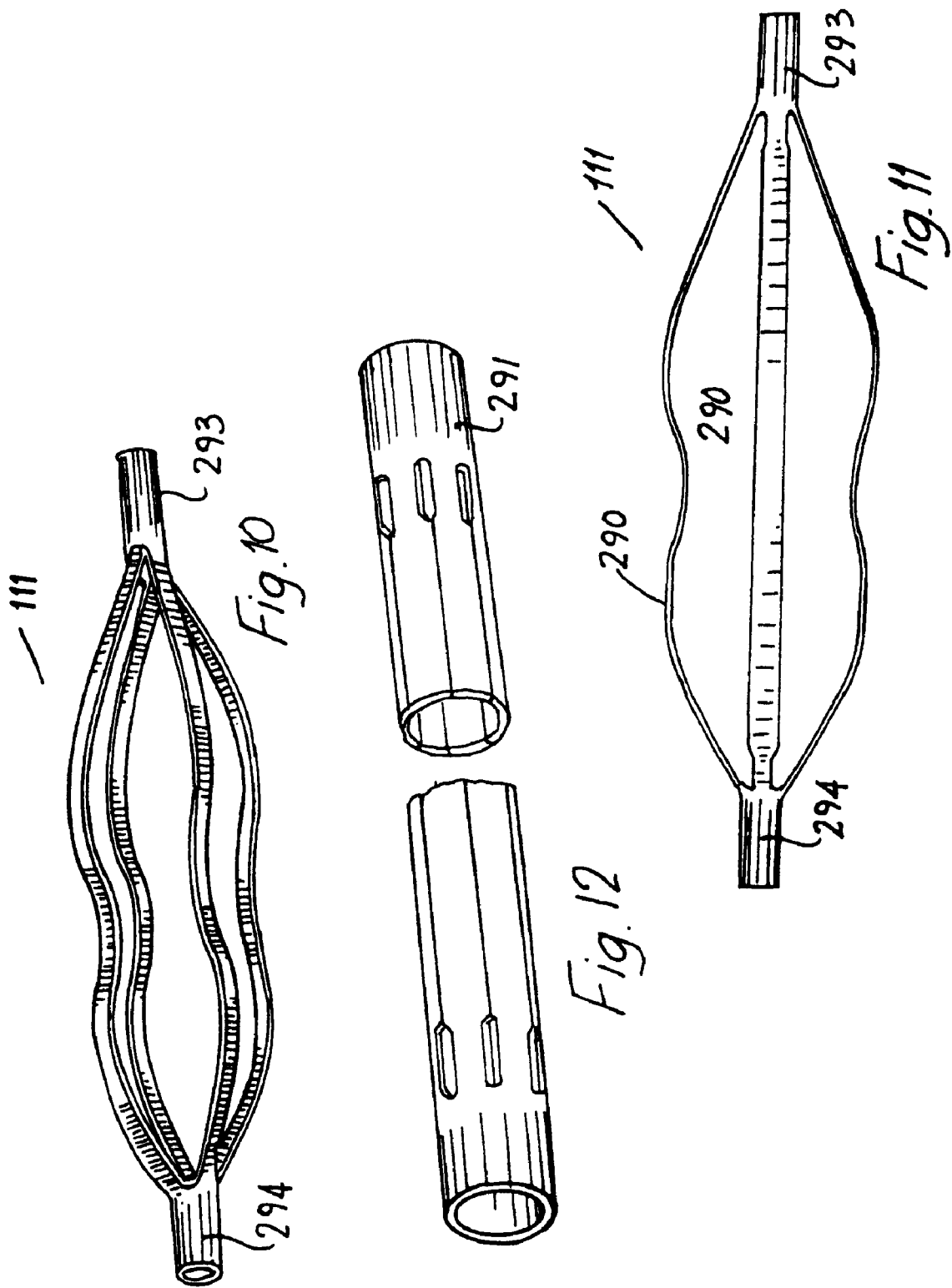

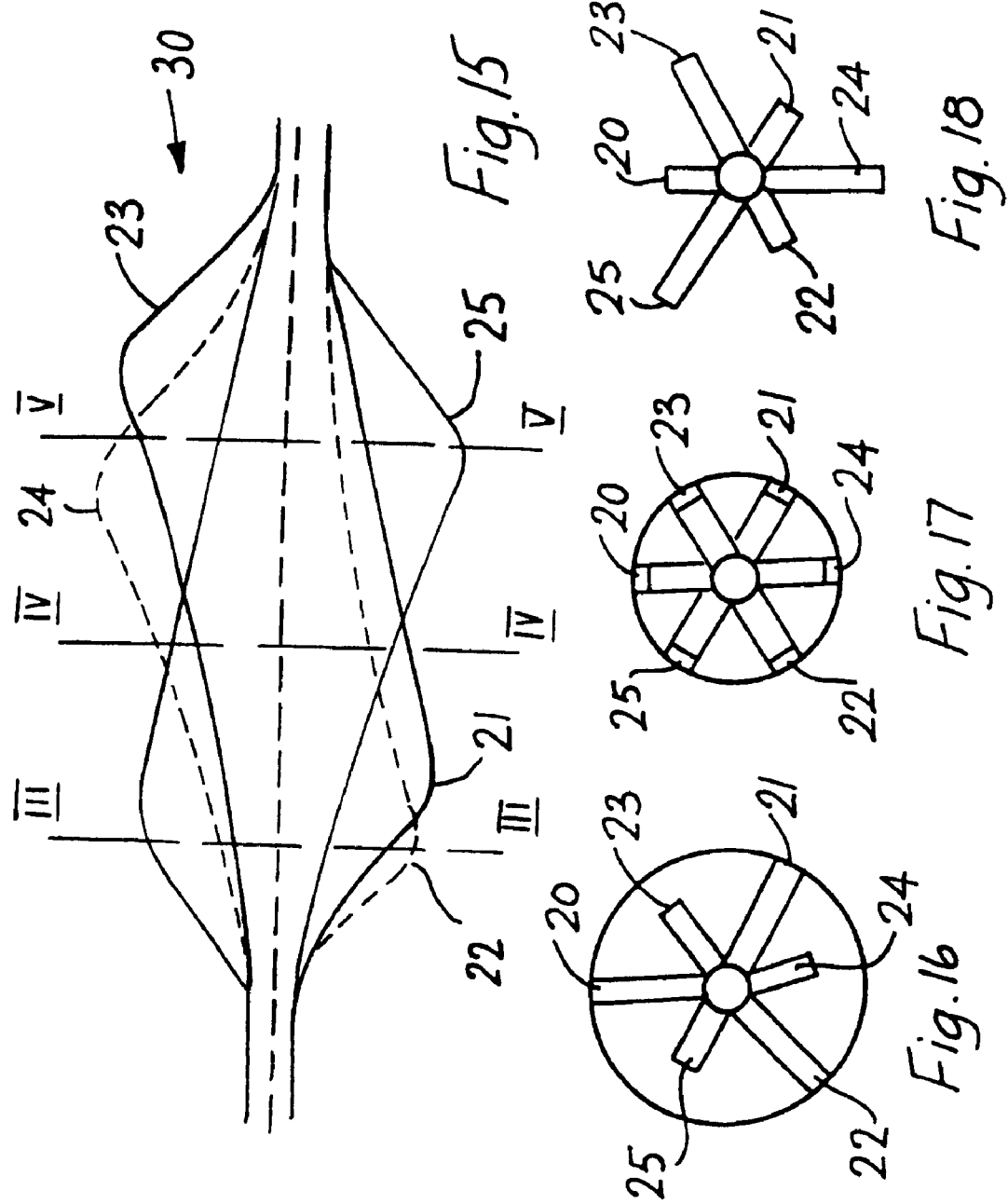

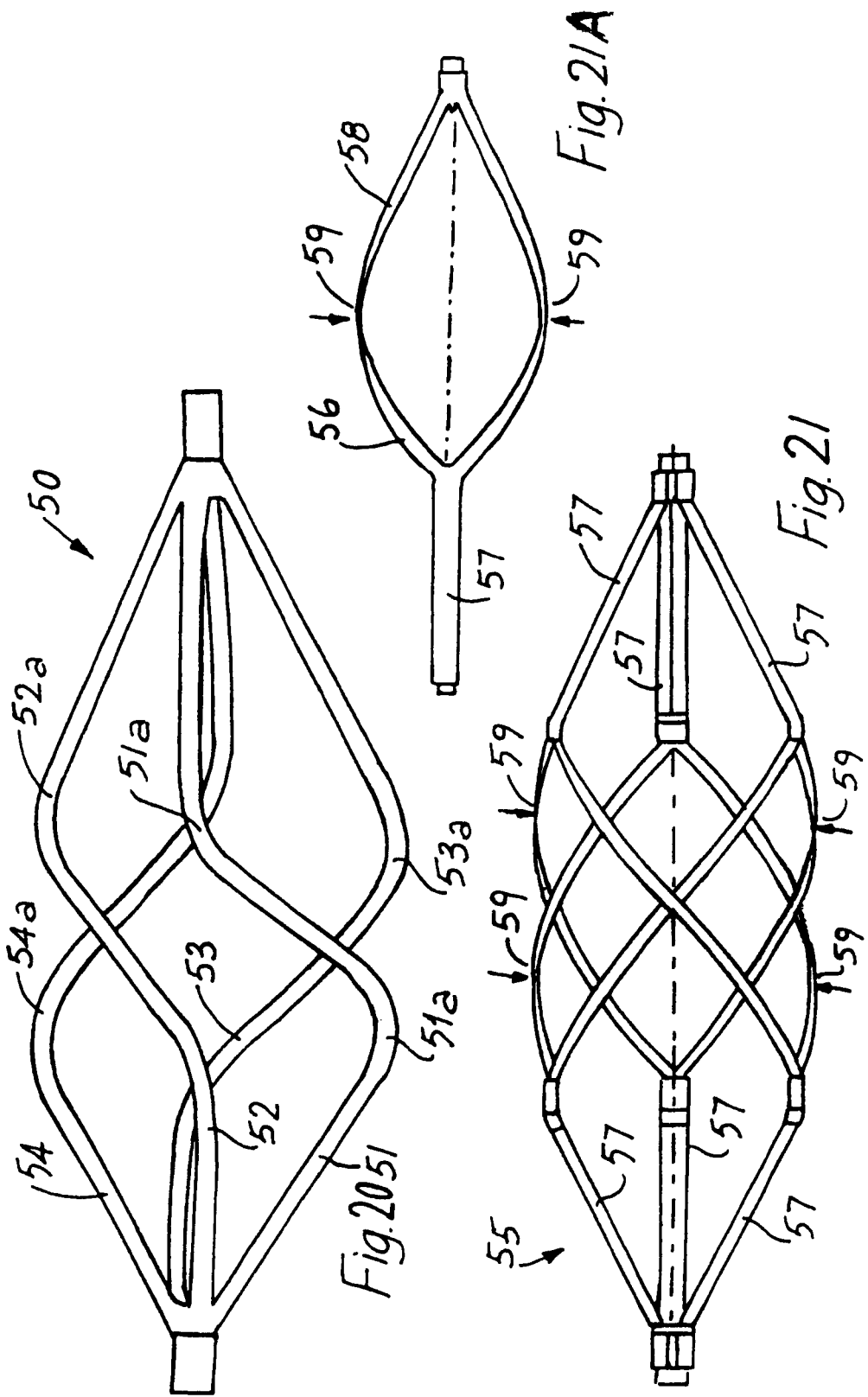

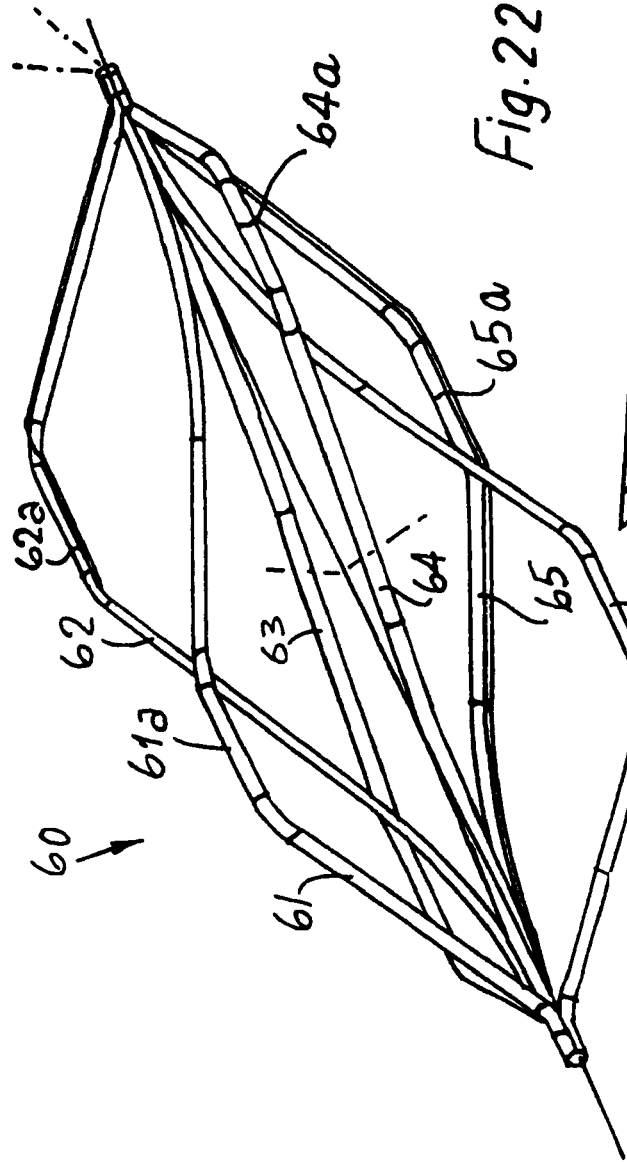
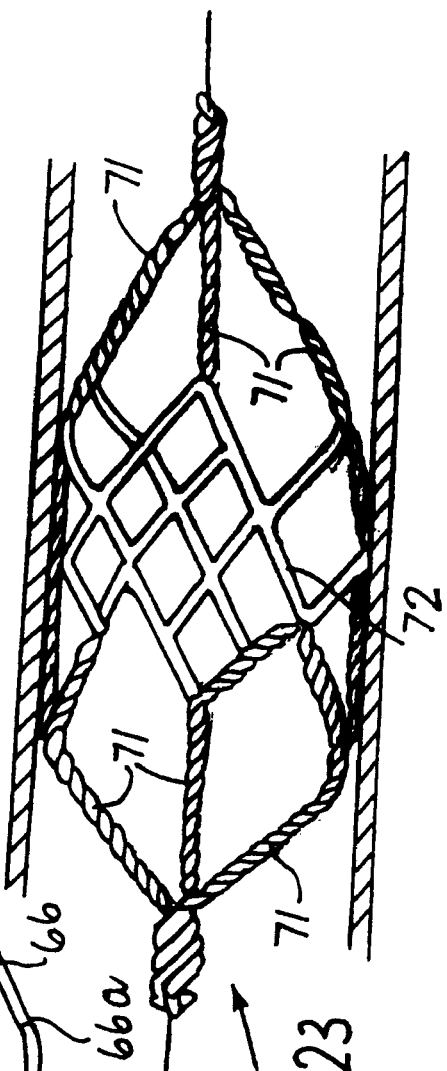

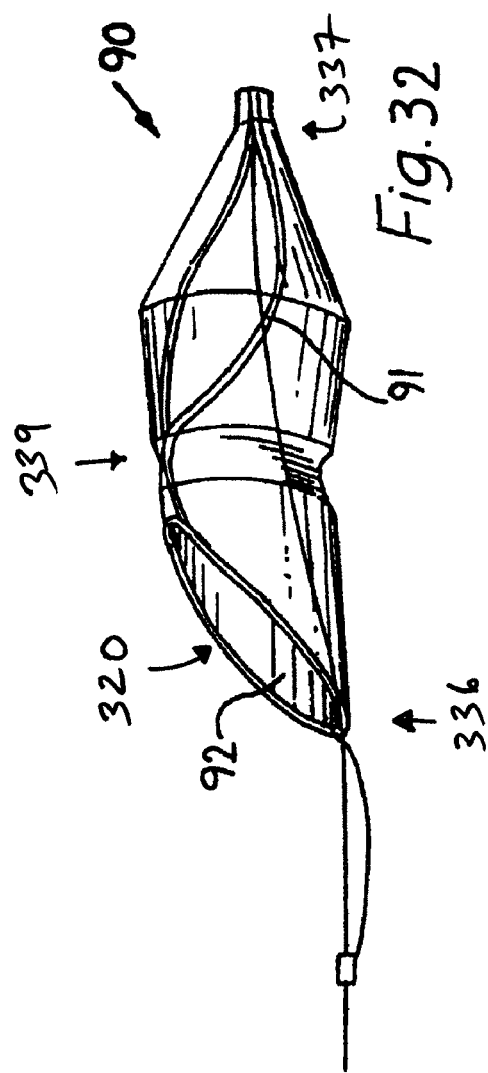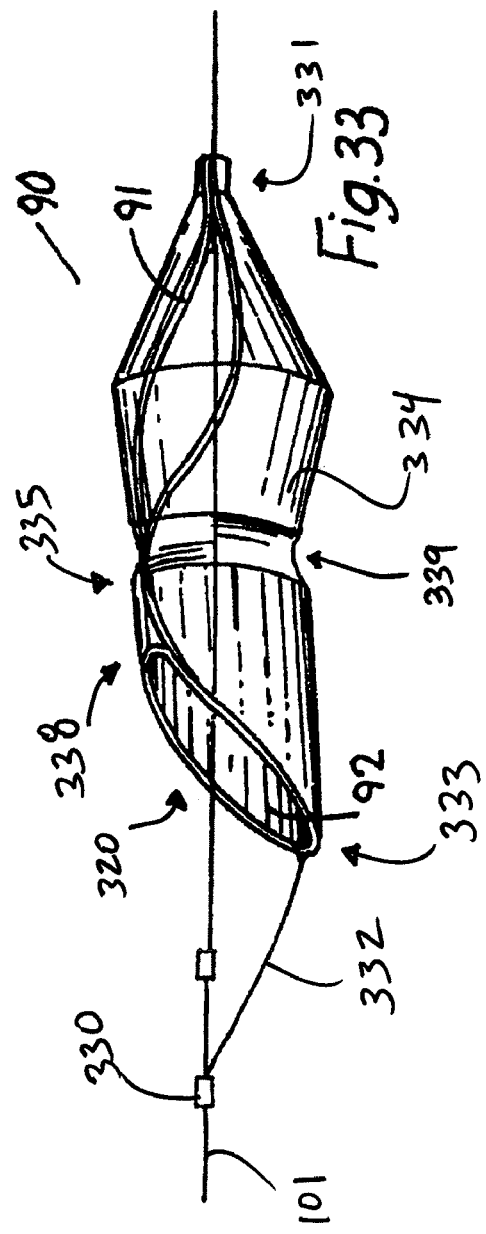

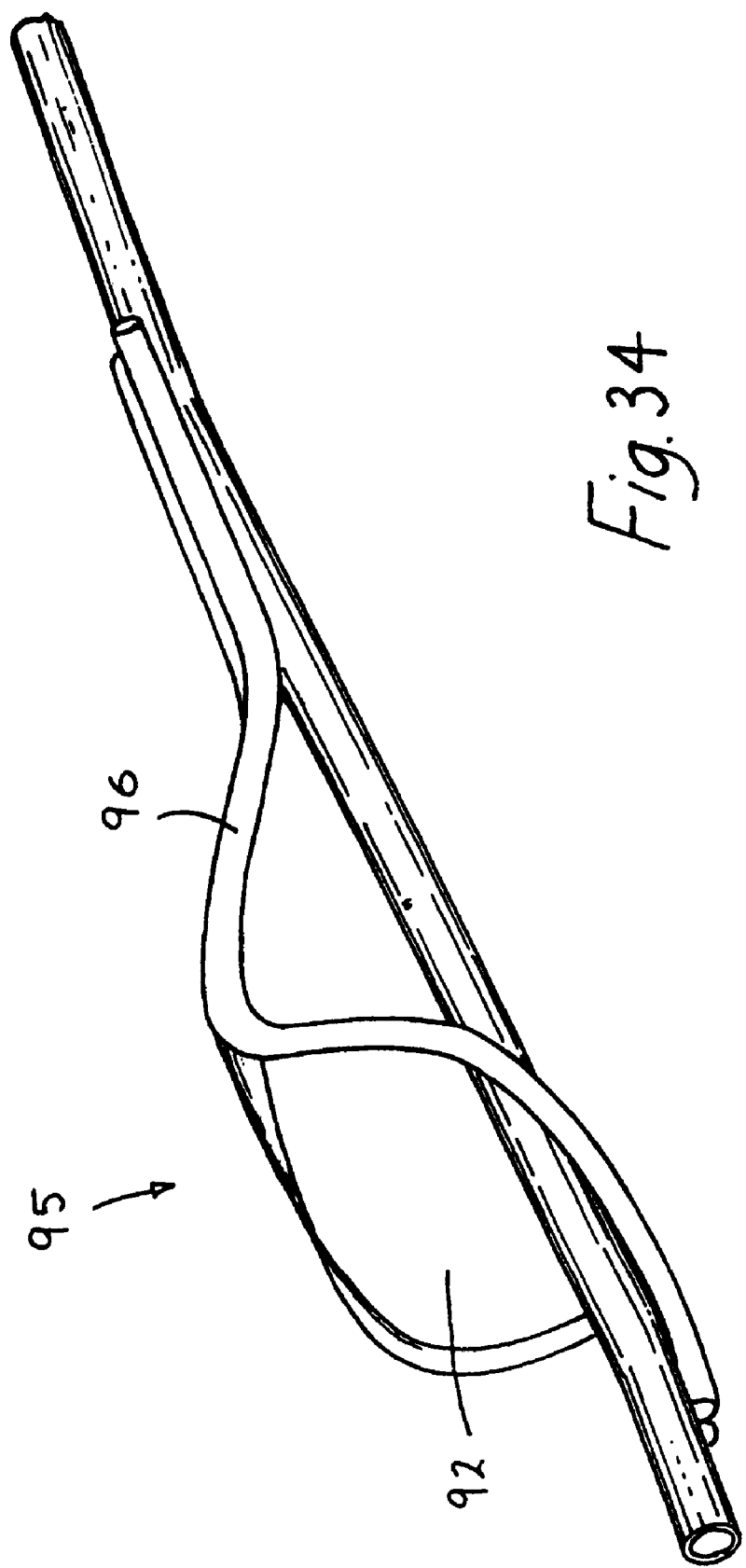

SUPPORT FRAME FOR AN EMBOLIC PROTECTION DEVICE

This application is a continuation of U.S. application Ser. No. 11/505,469 filed Aug. 17, 2006, which is a continuation of U.S. application Ser. No. 10/797,612 filed Mar. 11, 2004, now abandoned, which is a continuation of U.S. application Ser. No. 09/986,132 filed Nov. 7, 2001, now abandoned, which is a continuation of PCT/IE00/00054, filed May 8, 2000, and claims benefit under 35 U.S.C. §119 to International Application No. PCT/IE99/00035 filed on May 7, 1999, all of the disclosures of which are hereby incorporated by reference in their entirety.

BACKGROUND OF THE INVENTION

1. Field of the Invention

This invention relates to a filter element for a transcatheter embolic protection device.

2. Description of the Related Art

The invention is particularly concerned with filter elements for transcatheter embolic protection devices of the type described in our WO-A-9923976. One type of such embolic filter essentially comprises a filter body mounted on an associated collapsible support frame which can be collapsed by means of a catheter for deployment of the filter through a patient's vascular system. Upon retraction of the catheter the support frame and filter body expand outwardly from across a blood vessel within which the filter is positioned to filter blood flowing through the blood vessel.

The support structure is generally of superelastic or shaped memory material such as Nitinol™ which provides the circumferential pressure on expansion to secure the filter body in a close fit within the vessel.

It is important to achieve apposition of a filter body with the wall of the vessel in which the filter is deployed to ensure that there is no pathway between the filter body and the vessel wall through which embolic material could pass. This is not a simple issue in view of the wide variations in vessel geometry and the variable physical properties of a vessel lining at different locations even within a single vasculature.

When the filter element is being pulled through a small diameter conduit or opening for loading and retrieval, there are certain forces exerted on the support frame. The first is on entry of the proximal end into the tube and when the whole of the proximal end has been inserted into the tube and the distal end is about to be inserted into the catheter tube. Considerable loading forces are generated which in some cases require considerable retraction forces to overcome.

There is therefore a need to provide a support frame for a filter which will address these problems.

SUMMARY OF THE INVENTION

According to the invention there is provided an embolic protection device comprising:

a collapsible filter element for delivery through a vascular system of a patient;

the filter element comprising a collapsible filter body and a filter support frame contacting the filter body;

the collapsible filter body having an inlet end and an outlet end, the inlet end of the filter body having one or more inlet openings sized to allow blood and embolic material to enter the filter body, the outlet end of the filter body having a plurality of outlet openings sized to allow through passage of blood but to retain undesired embolic material within the filter body;

the filter support frame having a longitudinal axis and being movable between a collapsed position for movement through the vascular system and an extended outwardly projecting position to support the filter body in the expanded position;

the frame having a plurality of engagement segments, the engagement segments being spaced-apart longitudinally and transversely when the filter is in the deployed expanded configuration to urge the filter body into apposition with the vessel wall.

In one embodiment of the invention the engagement segments define at least one at least partially substantially helical engagement track.

Preferably the frame comprises a number of frame elements, at least some of the frame elements having an engagement segment. Ideally at least some of the frame elements are interconnected.

In another embodiment of the invention the frame has an intermediate section and a proximal section extending from the intermediate section, the engagement segments being provided in the intermediate section of the frame. Preferably the proximal section of the frame extends radially inwardly of the intermediate section and defines at least one inlet hole to accommodate inflow of embolic material to be captured in the filter. Most preferably the proximal section of the frame has a proximal mounting for mounting on a filter carrier. Ideally the proximal mounting is substantially tubular.

The proximal mounting may be offset with respect to the longitudinal axis of the support frame.

In a particularly preferred embodiment, the proximal section of the frame is flexible with respect to the intermediate section of the frame. Ideally the proximal section of the frame comprises a number of proximal elements, at least some of which are of a flexible material. Most preferably the proximal section of the frame comprises a plurality of flexible elements of relatively low column strength which are movable individually and independently of the intermediate section between taut and slack configuration.

In a further embodiment of the invention the frame includes a distal section extending from the intermediate section, the distal section of the frame being flexible with respect to the intermediate section of the frame. Preferably the distal section of the frame includes a plurality of flexible elements of relatively low column strength which are movable individually and independently of the intermediate section between taut and slack configurations. Ideally the flexible elements are thread-like elements. Most preferably at least some of the flexible elements define tethers.

In another preferred embodiment of the invention the frame has a distal section extending from the intermediate section. Preferably the distal section of the frame extends radially inwardly of the intermediate section. Ideally the distal section of the frame has a distal mounting for mounting on a filter carrier.

The distal mounting is preferably substantially tubular.

In one embodiment of the invention the distal mounting is offset with respect to the longitudinal axis of the support frame.

Preferably the distal section of the frame is flexible with respect to the intermediate section of the frame.

At least the intermediate section of the support frame may be formed from wire.

Alternatively at least the intermediate section of the support frame may be formed by a slotted tube.

In a preferred embodiment at least the intermediate section of the support frame is an elastic, superelastic and/or a shaped memory material. Ideally at least the intermediate section of the support frame is of Nitinol™.

Desirably the included angle defined between adjacent frame elements is less than 90°. Most preferably the included angle is less than 60°.

In a further preferred embodiment at least a portion of a support frame element is offset from the longitudinal axis by an angle of less than 45° in the expanded configuration.

Desirably a support frame element is offset from the longitudinal axis by an angle of less than 10° when the frame is in the collapsed configuration. Most preferably a support frame element is offset from the longitudinal axis by angles of less than 5° when the frame is in the collapsed configuration.

Ideally the engagement segments are defined by segments of a single frame element. The frame element is preferably at least partially of helical shape.

Desirably the collapsible filter body is mounted to the support frame.

In another aspect the invention provides an embolic protection device comprising:
- a collapsible filter element for delivery through a vascular system of a patient;
- the filter element comprising a collapsible filter body and a filter support frame contacting the filter body;
- the collapsible filter body having an inlet end and an outlet end, the inlet end of the filter body having one or more inlet openings sized to allow blood and embolic material to enter the filter body, the outlet end of the filter body having a plurality of outlet openings sized to allow through passage of blood but to retain undesired embolic material within the filter body;
- the filter support frame having a longitudinal axis and being movable between a collapsed position for movement through the vascular system and an extended outwardly projecting position to support the filter body in the expanded position;
- the frame having an intermediate section and a proximal section extending from the intermediate section; and
- the proximal section of the frame being flexible with respect to the intermediate section of the frame.

In one embodiment of the invention the proximal section of the frame comprises a plurality of flexible elements of relatively low column strength which are movable individually and independently of the intermediate section between taut and slack configuration.

In a preferred embodiment the frame includes a distal section extending from the intermediate section, the distal section of the frame being flexible with respect to the intermediate section of the frame. Preferably the distal section of the frame includes a plurality of flexible elements of relatively low column strength which are movable individually and independently of the intermediate section between taut and slack configurations. Ideally the flexible elements are thread-like elements.

Most preferably at least some of the flexible elements define tethers.

BRIEF DESCRIPTION OF THE DRAWINGS

The invention will be more clearly understood by the following description of some of the embodiments thereof, given by way of example only, with reference to the accompanying drawings, in which:

FIG. 2 is a schematic sectional elevational view of the embolic protection device of FIG. 1;

FIG. 3 is a detailed sectional view of a portion of the device of FIG. 1;

FIG. 4 is a longitudinal cross-sectional view of the device of FIG. 1;

FIG. 5 is a cross-sectional view of a distal end of the device of FIG. 1;

FIG. 6 is a view on the line A-A in FIG. 5;

FIG. 7 is a perspective view of a filter body of the device of FIGS. 1 to 6;

FIG. 8 is a side elevational view of the filter body of FIG. 7;

FIG. 9 is a view of a proximal end of the filter body;

FIG. 10 is a perspective view of a support frame of the device of FIGS. 1 to 6;

FIG. 11 is a side elevational view of the support frame;

FIG. 12 is a perspective view illustrating the manufacture of the support frame;

FIG. 15 is a longitudinal cross-sectional view of a support frame of the filter element of FIG. 14;

FIG. 16 is a cross-sectional view on the line III-III of FIG. 15;

FIG. 17 is a cross-sectional view on the line IV-IV of FIG. 15;

FIG. 18 is a cross-sectional view on the line V-V of FIG. 15;

FIG. 20 is a side elevational view of a filter support frame according to another embodiment of the invention;

FIG. 21 is a side elevational view of another support frame of the invention;

FIG. 21A is a side view of one support element of the frame of FIG. 21;

FIG. 22 is a perspective view of another support frame;

FIG. 23 is a longitudinal cross-sectional view of a further support frame, in a deployed use configuration;

FIGS. 32 and 33 are perspective views of a support frame in different positions of use;

FIG. 34 is a perspective view of a further support frame of the invention; and

DETAILED DESCRIPTION OF THE INVENTION

Figure 1:
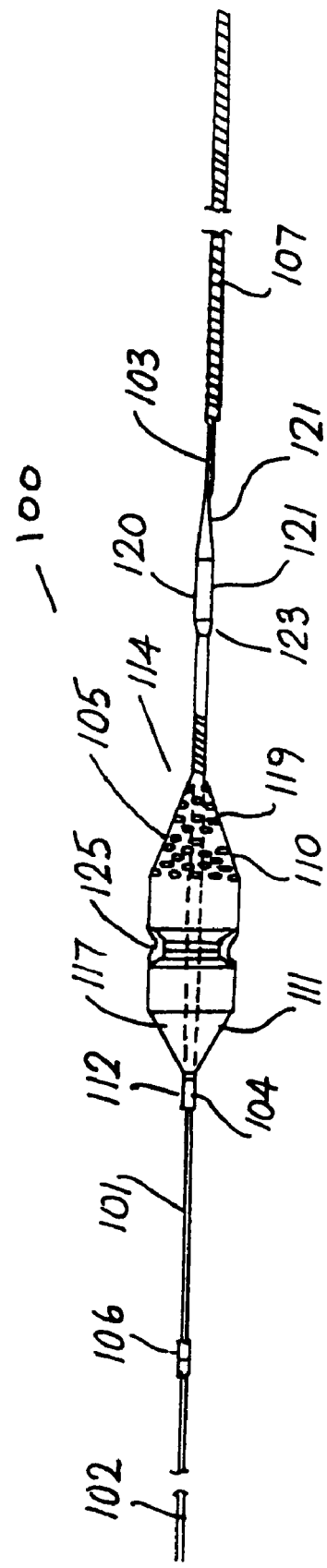
FIG. 1 is a partially sectioned elevational view of an embolic protection device.
Figure 13:
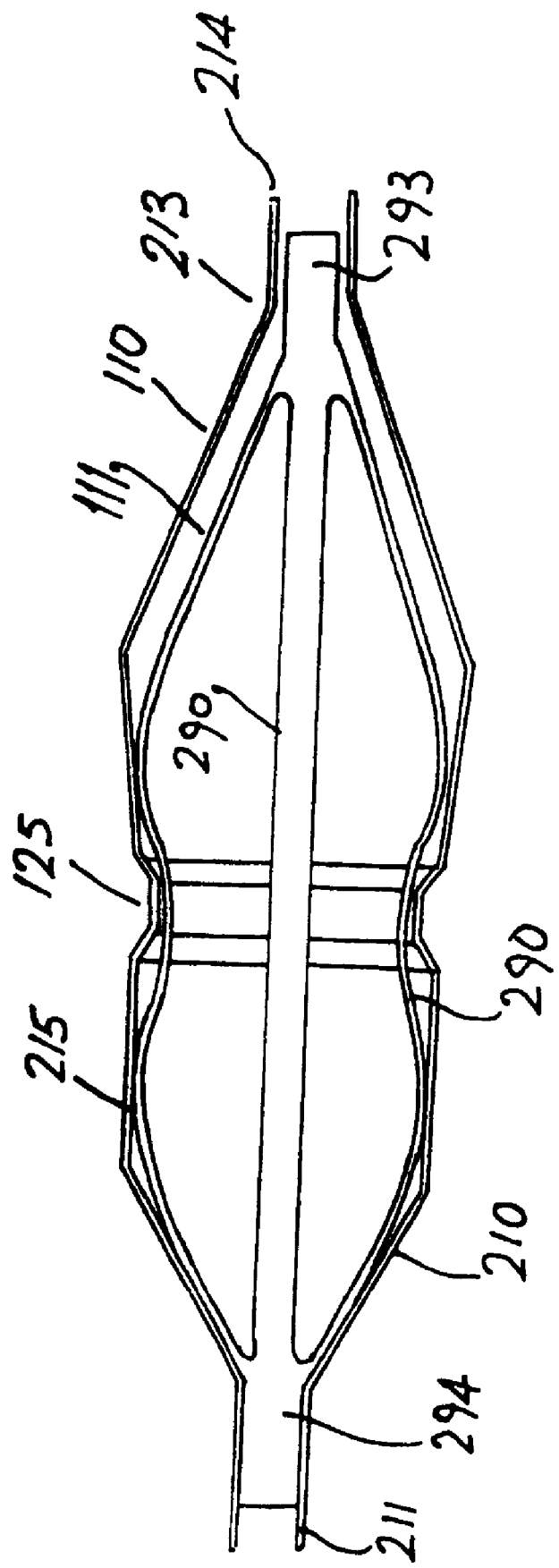
FIG. 13 is a view of the support frame and filter element assembly.
Figure 14:
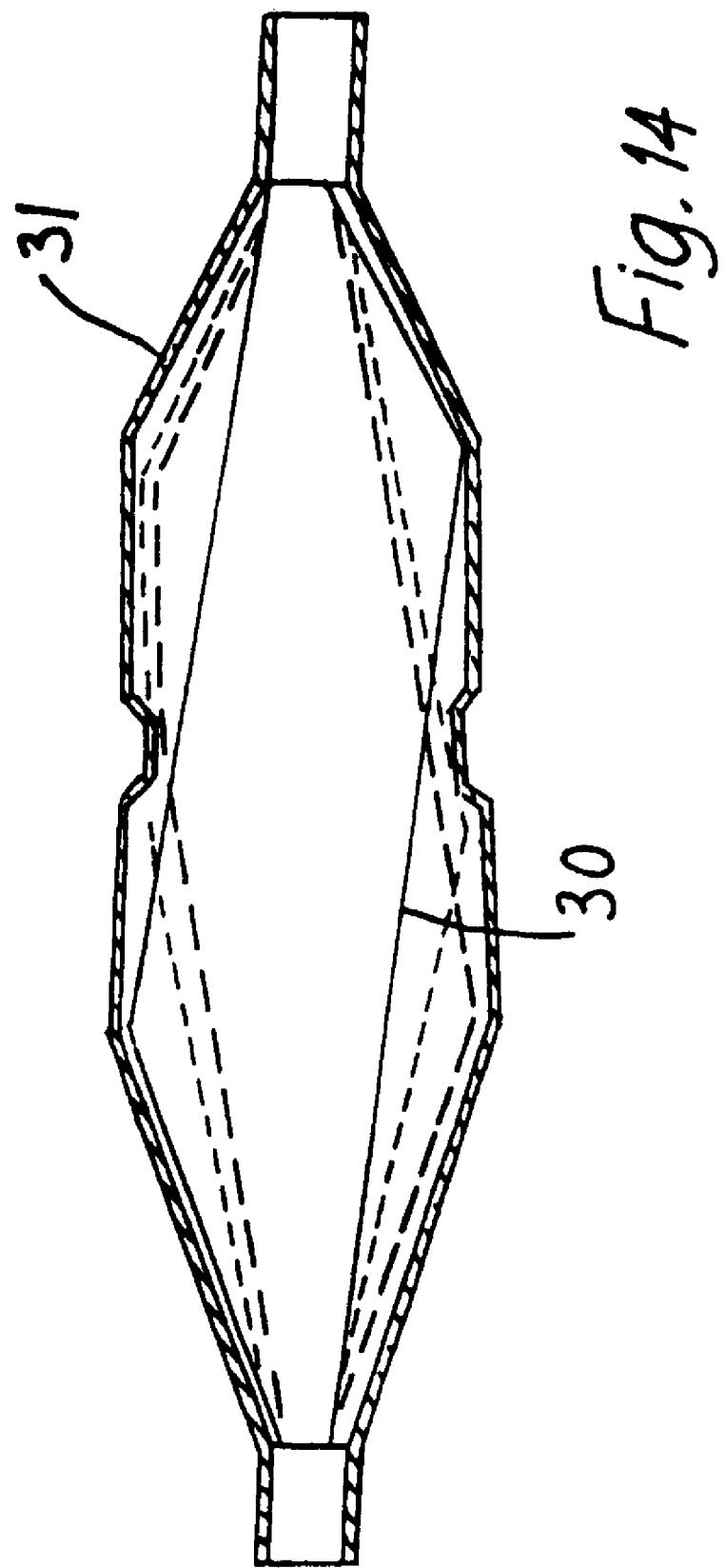
FIG. 14 is a longitudinal cross-sectional view of a filter element according to the invention.

Referring to FIGS. 1 to 13 there is illustrated an embolic protection device as described in our WO-A-9923976 indicated generally by the reference number 100. The device 100 has a guidewire 101 with a proximal end 102 and a distal end 103.

A tubular sleeve 104 is slidably mounted on the guidewire 101. A collapsible filter 105 is mounted on the sleeve 104, the filter 105 being movable between a collapsed stored position against the sleeve 104 and an expanded position as shown in the drawings extended outwardly of the sleeve 104 for deployment in a blood vessel.

The sleeve 104 is slidable on the guidewire 101 between a pair of spaced-apart end stops, namely an inner stop 106 and an outer stop which in this case is formed by a spring tip 107 at the distal end 103 of the guidewire 101.

The filter 105 comprises a filter body 110 mounted over a collapsible support frame 111. The filter body 110 is mounted to the sleeve 104 at each end, the body 110 being rigidly attached to a proximal end 112 of the sleeve 104 and the body 110 being attached to a collar 115 which is slidable along a distal end 114 of the sleeve 104. Thus the distal end of the body 110 is longitudinally slidable along the sleeve 104. The support frame 111 is also fixed at the proximal end 112 of the sleeve 104. A distal end 116 of the support frame 111 is not attached to the sleeve 104 and is thus also free to move longitudinally along the sleeve 104 to facilitate collapsing the support frame 111 against the sleeve 104. The support frame 111 is such that it is naturally expanded as shown in the drawings and can be collapsed inwardly against the sleeve 104 for loading in a catheter 118 or the like.

The filter body 105 has large proximal inlet openings 117 and small distal outlet openings 119. The proximal inlet openings 117 allow blood and embolic material to enter the filter body, however, the distal outlet openings 119 allow through passage of blood but retain undesired embolic material within the filter body.

An olive guide 120 is mounted at a distal end of the sleeve 104 and has a cylindrical central portion 121 with tapered ends 122, 123. The distal end 122 may be an arrowhead configuration for smooth transition between the catheter and olive surfaces. The support frame 111 is shaped to provide a circumferential groove 125 in the filter body 110. If the filter is too large for a vessel, the body may crease and this groove 125 ensures any crease does not propagate along the filter.

Enlarged openings are provided at a proximal end of the filter body 110 to allow ingress of blood and embolic material into an interior of the body 110.

In use, the filter 105 is mounted in a collapsed state within a distal end of the catheter 118 and delivered to a deployment site. When the filter is correctly positioned the catheter 118 is retracted allowing the support frame 111 to expand expanding the filter body 110 across the vessel in which the filter is mounted. Blood and emboli can enter the enlarged openings at a proximal end of the filter body 110. The blood will pass through the filter wall, however, the openings or pores in the filter are sized so as to retain the embolic material. After use the catheter is delivered along the guidewire 101 and slid over the filter 105 engaging the proximal inlet end 112 first to close the openings and then gradually collapsing the filter body against the sleeve 104 as the catheter 118 advances over the filter 105. Once the filter 105 is fully loaded in the catheter 118, it can then be withdrawn.

It will be noted that a proximal end of the filter is fixed and a distal end of the filter is longitudinally movable along the sleeve to facilitate collapsing of the filter body.

Further, the catheter engages the proximal end of the filter body first thus closing the filter body inlet and preventing escape of embolic material from the filter body as the filter body is being collapsed.

The outer filter body 110 is preferably of a resilient biocompatible elastomeric material. The material may be a polyurethane based material. There are a series of commercially available polyurethane materials that may be suitable. These are typically based on polyether or polycarbonate or silicone macroglycols together with diisocyanate and a diol or diamine or alkanolamine or water chain extender. Examples of these are described in EP-A-461,375 and U.S. Pat. No. 5,621,065. In addition, polyurethane elastomers manufactured from polycarbonate polyols as described in U.S. Pat. No. 5,254,622 (Szycher) are also suitable.

The filter material may also be a biostable polycarbonate urethane article an example of which may be prepared by reaction of an isocyanate, a chain extender and a polycarbonate copolymer polyol of alkyl carbonates. This material is described in our WO-A-9924084. The filter material may be manufactured from a block and cut into a desired shape. However the filter is preferably formed by dipping a rod of desired geometry into a solution of the material which coats the rod. The rod is then dissolved. The final geometry of the filter may be determined in the dipping step or the final geometry may be achieved in a finishing operation. Typically the finishing operations involve processes such as mechanical machining operations, laser machining or chemical machining.

The filter body is of hollow construction and is formed as described above by dipping a rod in a solution of polymeric material to coat the rod. The rod is then dissolved, leaving a hollow body polymeric material. The rod may be of an acrylic material which is dissolved by a suitable solvent such as acetone.

The polymeric body thus formed is machined to the shape illustrated in FIGS. 1 to 13. The final machined filter body comprises an inlet or proximal portion 210 with a proximal neck 212, and outlet or distal portion 213 with a distal neck 214, and an intermediate portion 215 between the proximal and distal portions.

The inlet holes 117 are provided in the proximal portion 210 which allow the blood and embolic material to flow into the filter body. In this case the proximal portion 210 is of generally conical shape to maximize the hole size.

The intermediate portion 215 is also hollow and in this case is of generally cylindrical construction. This is important in ensuring more than simple point contact with the surrounding blood vessel. The cylindrical structure allows the filter body to come into soft contact with the blood vessel to avoid damaging the vessel wall.

The intermediate portion 215 is provided with a radial stiffening means, in this case in the form of a radial strengthening ring or rim 220. The ring 220 provides localized stiffening of the filter body without stiffening the material in contact with the vessel. Such an arrangement provides appropriate structural strength so that line apposition of the filter body to the vessel wall is achieved. It is expected that other geometries of stiffening means will achieve a similar result.

The tubular intermediate portion 215 is also important in maintaining the stability of the filter body in situ to retain captured emboli and to ensure that flow around the filter is minimized. For optimum stability we have found that the ratio of the axial length of the intermediate portion 215 of the filter body to the diameter of the intermediate portion 215 is preferably at least 0.5 and ideally greater than 1.0.

The collapsible support frame 111 has four foldable arms 290 which are collapsed for deployment and upon release extend outwardly to expand the filter body 110.

The support frame 111 can be manufactured from a range of metallic or polymeric components such as a superelastic or shape memory alloy like Nitinol™ or a shape memory polymer or a shaped stainless steel or metal with similar properties that will recover from the deformation sufficiently to cause the filter body 110 to open.

The support frame may be formed as illustrated in FIG. 12 by machining slots in a tube 291 of superelastic material or shape memory alloy such as Nitinol™. On machining, the unslotted distal end of the tube forms a distal collar 293 and the unslotted proximal end of the tube forms a proximal collar 294. In use, the distal collar 293 is slidably moveable along the tubular sleeve 104 which in turn is slidably mounted on the guidewire 101 for deployment and retrieval. The proximal collar 294 is fixed relative to the tubular sleeve 104.

Alternatively, the construction may be made entirely of wires interconnected at various points.

To load the filter, the sub assembly of the support frame and filter body is pulled back into the catheter 118 to engage the distal stop 107. The support arms 290 are hinged inwardly and the distal collar 293 moves forward along the tubular sleeve 104. As the support arms 290 enter the catheter 118 the filter body 110 stretches as the filter body collar 115 slides along the tubular sleeve 104 proximal to the olive 120. On deployment, the catheter 118 is retracted proximally along the guidewire 101 initially bringing the collapsed filter assembly with it until it engages the proximal stop 106. The catheter sleeve then begins to release the filter freeing the support arms 290 to expand and the filter body apposes the vessel wall.

For retrieval, a retrieval catheter is introduced by sliding it over the guidewire 101 until it is positioned at the proximal end of the filter body and support frame. Pulling the guidewire 101 will initially engage the distal stop 107 with the filter element and begin to pull it into the retrieval catheter. The initial travel into the delivery catheter acts to close the proximal openings of the filter element, thus entrapping the embolic load. As the filter continues to be pulled back the filter body and the support frame are enveloped in the retrieval catheter. The collapsed filter may then be removed from the patient.

Various support frames according to the invention are described below with reference to FIGS. 14 to 35. In each case the frame has a plurality of engagement segments formed on one or more support arms (some of which may be interconnected). The engagement segments are spaced-apart longitudinally and transversely when the filter is in the deployed expanded configuration to urge the filter body into apposition with the vessel wall. The support frames of the invention provide apposition of the filter body to the wall of a vessel in which the filter is deployed. This is achieved while reducing the loading forces required to load the filter into a delivery catheter for deployment and for loading the filter into a retrieval catheter for retrieval of the filter together with any embolic material captured by the filter.

Referring to FIGS. 14 to 18 there is illustrated a support frame indicated generally by the reference numeral 30 for a filter 31. The filter support frame 30 comprises a plurality of support elements each of which extend in a longitudinal direction. Some of the support elements provide support for one portion of the filter body 31 and some provide support for another portion of the filter body 31. In this case there are six support arms, three arms 30, 31, 22 providing support for a proximal end of the filter body 31 and three arms 23, 24, 25 providing support for a distal end of the filter body 31. The support arms 20, 21, 22, 23, 24, 25 each have engagement sections to engage the filter body. The engagement segments are spaced-apart longitudinally and transversely when the filter is in the deployed expanded configuration. Apposition is thereby improved while loading forces are greatly reduced allowing the filter to be more easily loaded and retrieved.

Figure 19:
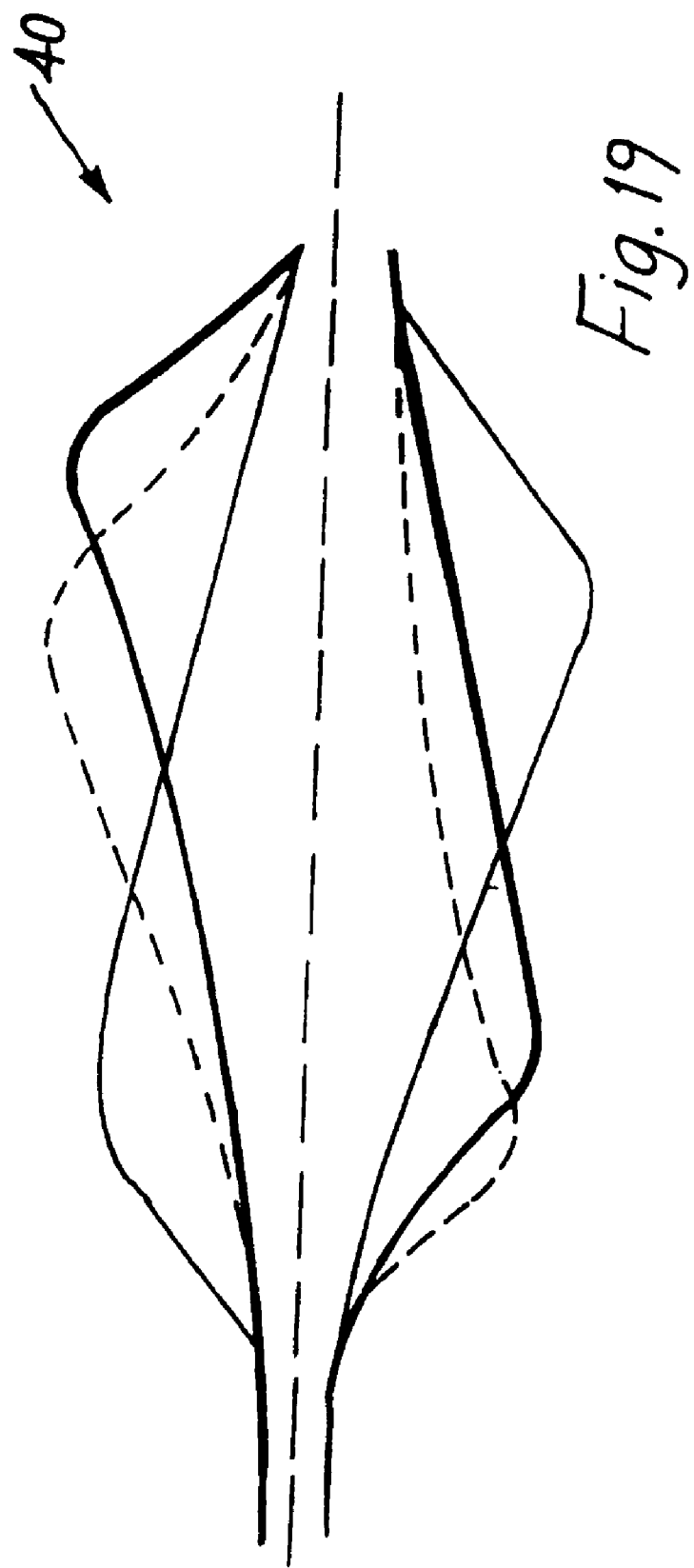
FIG. 19 is a longitudinal cross-sectional view of another support frame.

Referring to FIG. 19 there is illustrated another support frame 40 similar to that of FIGS. 14 to 18. In this case adequate support is provided while omitting the distal collar 293. This frame 40 is easily formed and the same principle may be applied to other frames as those described above and below.

Referring to FIG. 20 there is illustrated another support frame 50 which comprises four support arms 51, 52, 53, 54. Each of the arms 51, 52, 53, 54 is of at least partially helical shape and different engagement segments 51*a*, 52*a*, 53*a*, 54*a* of the arms are spaced-apart longitudinally and transversely when the filter is in the deployed expanded configuration illustrated. This arrangement is especially advantageous because it is relatively easily formed and provides excellent apposition with reduced loading forces.

Referring to FIG. 21 there is illustrated another support frame 55 according to the invention. The support frame 55 comprises six support elements 56, one of which is shown in FIG. 21A. Each element 56 includes a distal or proximal tether section 57 and a closed loop portion 58 extending from the tether section 57. The loops 58 have engagement sections 59 and the engagement sections of the frame are longitudinally and transversely spaced-apart to achieve apposition in a central section of the frame 55.

Referring to FIG. 22 there is illustrated a further support frame 60 comprising six separate support elements 61, 62, 63, 64, 65, 66 which are again arranged to provide engagement segments 61*a*, 62*a*, 63*a*, 64*a*, 65*a*, 66*a* which are longitudinally and transversely spaced-apart to provide apposition while requiring reduced loading forces.

Referring to FIG. 23 another support frame 70 of the invention is made from twisted wires of a shaped memory/superelastic material such as Nitinol™. In this there are four support elements, each provided by a twisted wire 71. The wires 71 are joined together by twisting at proximal and distal ends. The wires 71 are joined together in a central region between the distal and proximal ends to form a lattice-like structure 72 which defines a plurality of longitudinally and transversely spaced-apart engagement segments.

Figure 24:
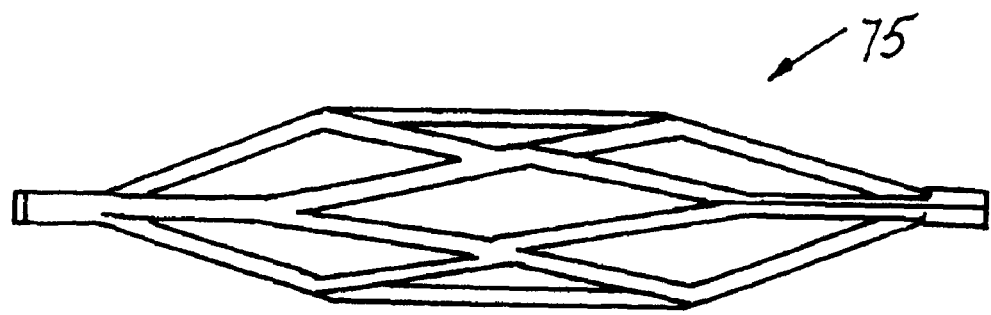
FIG. 24 is a side view of another support frame in a partially collapsed configuration.
Figure 25:
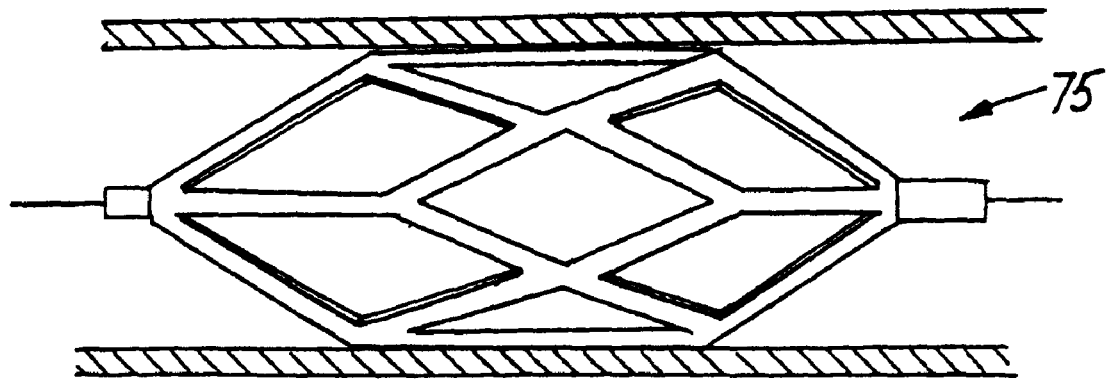
FIG. 25 is a longitudinal cross-sectional view of the support frame of FIG. 24 in a deployed use configuration.

Referring to FIG. 24 there is illustrated a support frame 75 which is in the form of a lattice-like arrangement to achieve substantial apposition to a vessel wall in use as illustrated in FIG. 25.

Figure 26:
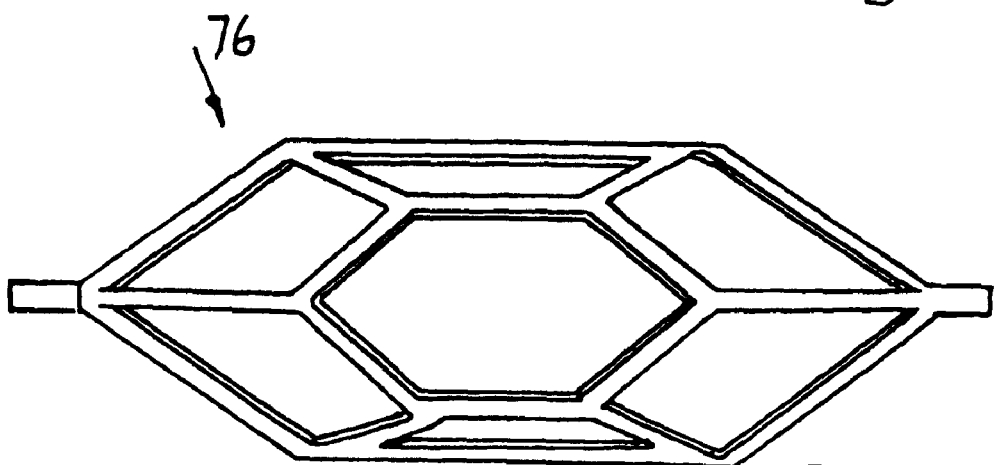
FIG. 26 is a side view of another support frame.

In FIG. 26 there is illustrated a support frame 76 similar to the frame 75 of FIGS. 24 and 25. In this case the lattice in a central region is of generally hexagonal shape.

Figure 27:
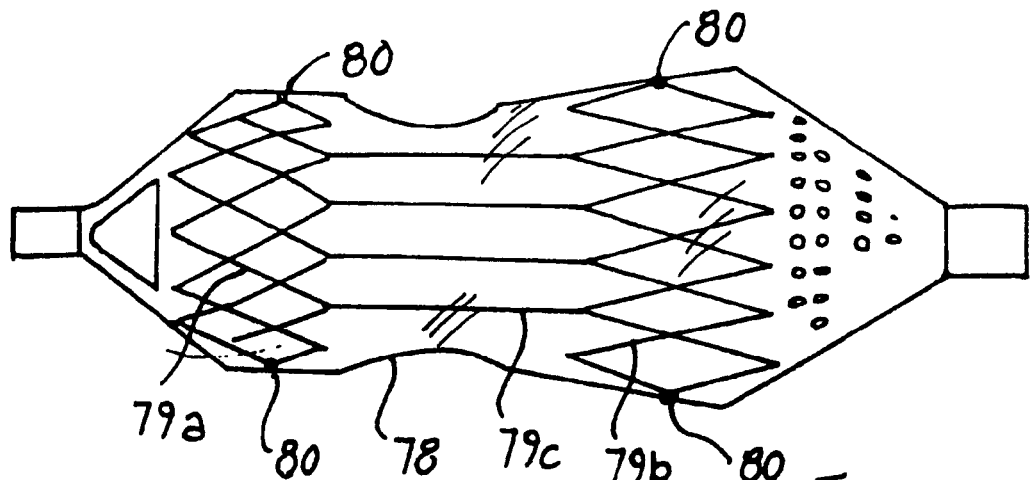
FIG. 27 is a side view of a still further support frame and filter of the invention.

Referring to FIG. 27 there is illustrated a filter comprising a filter membrane 78 supported by a support frame 79. The support frame 79 comprises a distal lattice portion 79*a*, a proximal lattice portion 79*b* and a series of interconnecting struts in a central portion 79*c*. In this case the support frame 79 is attached by connections 80 to the filter membrane 78. The filter support frame 79 is mounted to the filter body and is independent of the guidewire. Therefore lateral movement of the guidewire will not affect the position of the filter support frame and apposition will not be adversely affected by guidewire movement.

Figure 28:
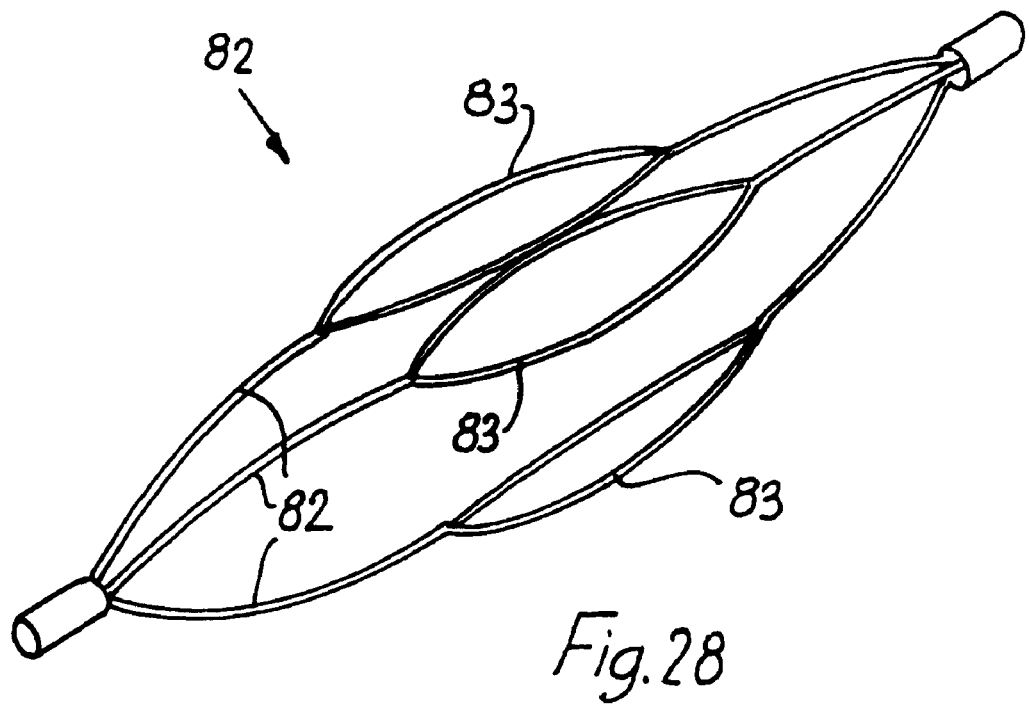
FIG. 28 is a perspective view of another support frame.

Referring to FIG. 28 another support frame 82 according to the invention comprises a number of frame elements which divide intermediate the proximal and distal ends into loops 83 which define engagement segments.

Figure 29:
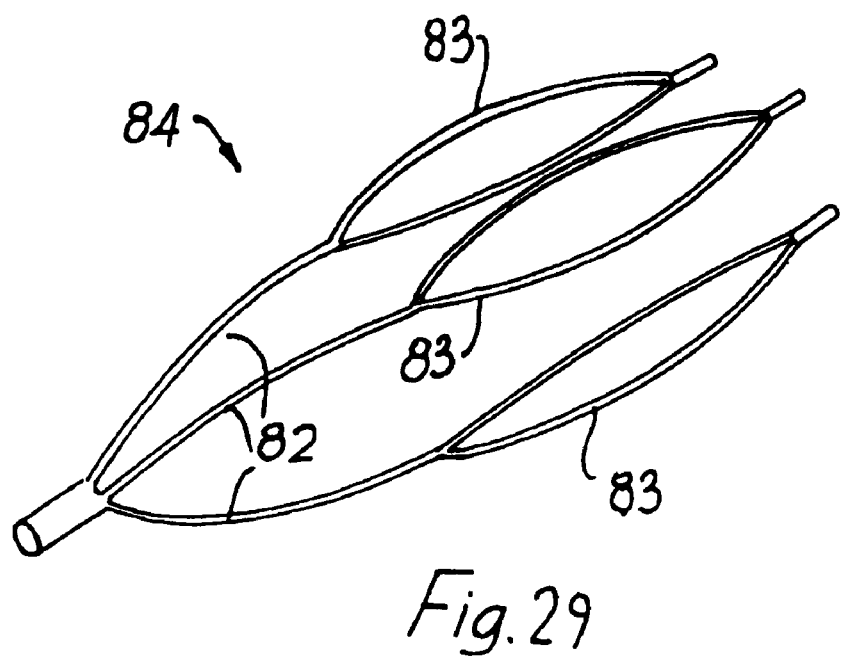
FIG. 29 is a perspective view of yet another support frame.

In FIG. 29 there is illustrated another support frame 85 similar to the frame of FIG. 28 and like parts are assigned the same reference numerals. In this case the frame elements 82 are not interconnected at the distal end.

Figure 30:
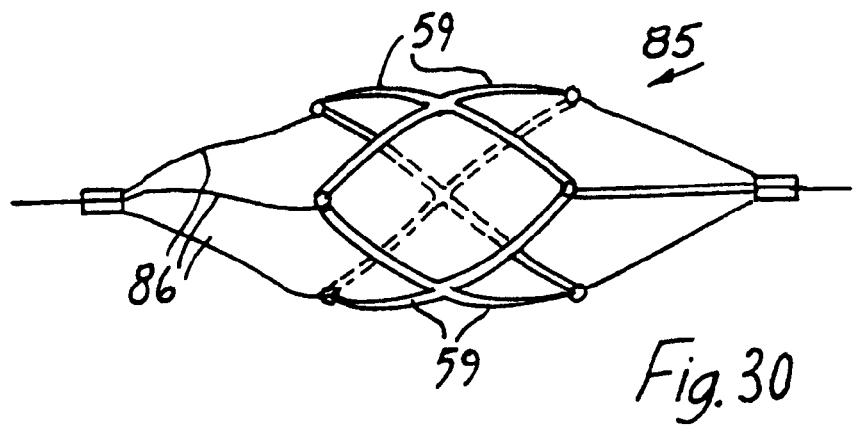
FIGS. 30 and 31 are side views of another support frame in different positions of use.
Figure 31:
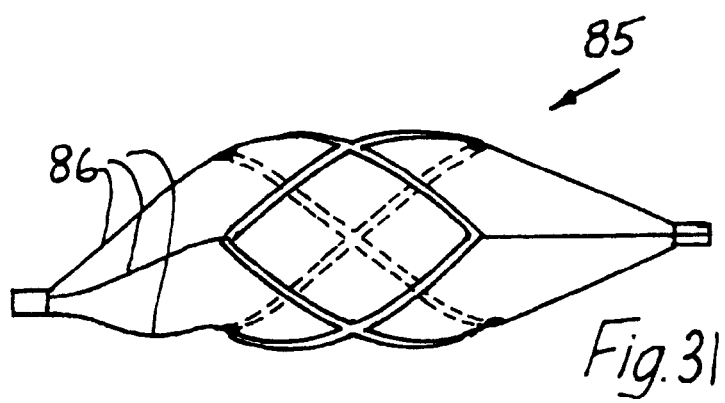

Referring now to FIGS. 30 and 31 there is illustrated another filter support frame 85 according to the invention which is similar to the embodiment of FIG. 21 described above and like parts are assigned the same reference numerals. In this case the filter frame is proximally connected by means of two or more, preferably three flexible, (low column strength) threads/monofilaments 86. The threads 86 may be moved individually and independently of the intermediate section between a slack and taut configuration. This allows for a greater freedom of movement of the guidewire relative to the center of the lumen without distorting the filter element. This is particularly advantageous in curved vasculatures where the guidewire may have the tendency to move away from the centre of the lumen, or in embodiments such as offset filters where the delivery of interventional catheters proximal to the filter may cause the guidewire to move towards the centre thus causing the filter to distort.

Referring to FIGS. 32 and 33 there is illustrated an offset filter 90 according to the invention. The frame may be of Nitinol™ wire of slotted tube configuration. One or more support elements 91 define a loop like structure 320 at an angle at the proximal end to define a proximal inlet hole 92. More specifically, as clearly shown in FIGS. 32 and 33, the loop structure 320 is in a plane that is transverse to the longitudinal axis of the filter 90, and the plane is tilted on an angle proximally to distally relative to a plane that would be transverse and perpendicular to the longitudinal axis of the filter, such that one end 333 of the loop structure 320 is set back proximally of the opposing end 338 of the loop structure 320. The design for the intermediate and the distal sections of the filter may vary. In the embodiment illustrated there are two support elements 91 which form a partial helical structure along the periphery of the filter membrane 334. The offset design allows for a single, large proximal hole diameter, thus enabling the capture of large emboli and also maximum space for blood flow within the filter. The guidewire 101 enters the filter through a proximal collar 330 off the center of the vasculature. Further, a proximal end of the support frame 333 is coupled to the proximal collar 330 via a flexible tether 332, the tether being movable independently of the support frame. Each of the two support elements 91 have a proximal end shown generally by arrow 336, and a distal end shown generally by arrow 337, the two support elements defining a loop structure 320 by joining the proximal ends of each of the two support elements and joining an intermediate point of each of the two support elements shown generally by arrow 335, the loop structure 320 extending around and supporting the inlet hole of the filter membrane. The two support elements 91 may be formed by a single bent wire. A distal coupling part 331 is also included for directly coupling the support frame to a guidewire, and the distal ends 337 of the two supports elements are coupled to the distal coupling part. The filter membrane 334 has a circumferential groove 339 formed in an intermediate section of the filter membrane between the proximal end and the distal end of the filter, similar to the embodiment shown in FIGS. 1, 4, 5, 7 and 9. If the filter is too large for a vessel, the body may crease and this groove 339 ensures any crease does not propagate along the filter.

Figure 35:
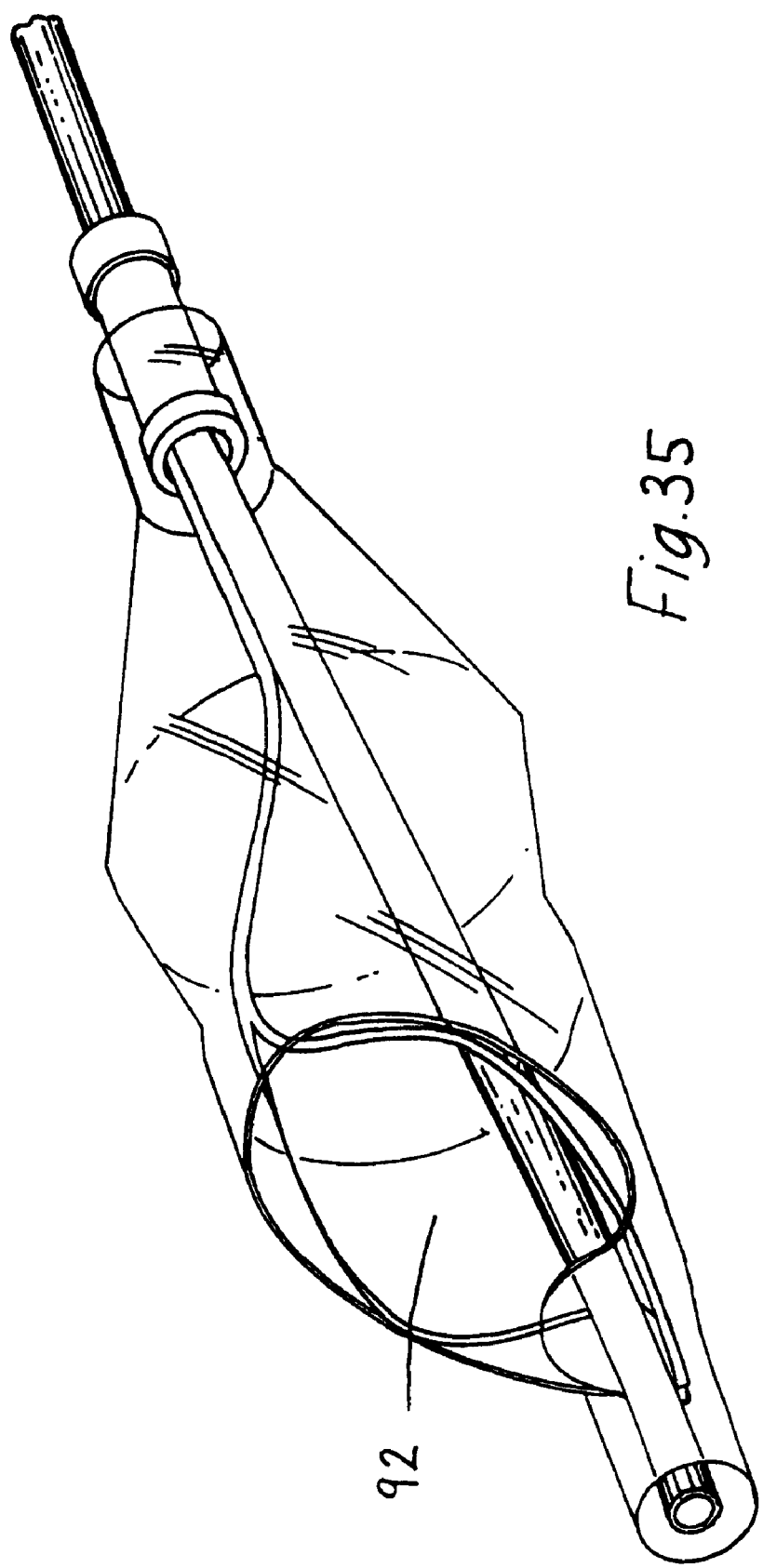
FIG. 35 is a perspective view of the support frame of FIG. 34 and an associated filter.

Referring to FIGS. 34 and 35 there is illustrated another offset filter 95 according to the invention which is similar to the filter of FIGS. 32 and 33. In this case there is a single support element 96. The membrane is self-supported at the distal end.

The support frame may comprise one or a number of support elements extending in a substantially longitudinal direction. In a preferred embodiment, at least a portion of the longitudinal support element is offset by less than 45° from its longitudinal axis. This provides circumferential apposition while greatly reducing the loading forces. In its collapsed configuration, the support elements are preferably offset within 10° preferably within 5° of the longitudinal axis.

It will be appreciated that the local stiffeners of the support element can be reduced in the collapsed state by having an undulating/curved section about which the collapsed filter can bend. This provides increased flexibility during delivery in an arrangement such as that of FIG. 20 described above.

The invention is not limited to the embodiments hereinbefore described which may be varied in both construction and detail.

What is claimed is:

1. An embolic protection filter comprising:
a shaped polymeric membrane having a proximal inlet end and a distal outlet end, the inlet end of the filter membrane having a single inlet hole sized to allow blood and embolic material enter the filter membrane, the outlet end of the filter membrane having a plurality of outlet openings sized to allow through passage of blood but to retain undesired embolic material within the filter membrane;
a support frame to support the filter membrane in an expanded position;
a proximal collar for coupling the filter to a guidewire, a proximal end of the support frame coupled to the collar via a flexible tether, the tether being movable independently of the support frame; and
a distal coupling part for directly coupling the support frame to a guidewire; wherein
the proximal collar is separate from and longitudinally spaced apart from the distal coupling part; and
the support frame couples the proximal collar to the distal coupling part.

2. A filter as claimed in claim 1, wherein the proximal collar and the distal coupling part each define a lumen therethrough through which a guidewire is insertable.

3. A filter as claimed in claim 2, wherein the proximal collar and the distal coupling part are movable relative to the guidewire.

4. A filter as claimed in claim 3, wherein the proximal collar and the distal coupling part are rotatable relative to the guidewire.

5. A filter as claimed in claim 3, wherein the proximal collar and the distal coupling part are movable longitudinally relative to the guidewire.

6. A filter as claimed in claim 2, wherein an external face of the guidewire slidably contacts an internal face of the proximal collar.

7. A filter as claimed in claim 2, wherein when the filter is in the expanded position for filtering blood flowing through the vasculature, a middle portion of the inlet hole is radially offset from the path of the guidewire.

8. A filter as claimed in claim 1, wherein the tether has a low column strength relative to the support frame.

9. A filter as claimed in claim 1, wherein when the filter is in the expanded position for filtering blood flowing through the vasculature, the proximal collar is radially offset from the center of the vasculature.

10. A filter as claimed in claim 1, wherein a circumferential groove is formed in an intermediate section of the filter membrane between a proximal end and a distal end of the filter.

11. A filter as claimed in claim 1, wherein the support frame comprises two support elements which form a partial helical structure along the periphery of the filter membrane, each of the two support elements having a proximal end and a distal end, the two support elements defining a loop structure by joining the proximal ends of each of the two support elements and joining an intermediate point of each of the two support elements, the loop structure extending around and supporting the inlet hole of the filter membrane.

12. A filter as claimed in claim 11, wherein in the expanded position, the loop structure is in a plane that is transverse to the longitudinal axis of the filter, and the plane is tilted on an angle proximally to distally relative to a plane that is transverse and perpendicular to the longitudinal axis of the filter, such that one end of the loop structure is set back proximally of the opposing end of the loop structure.

13. A filter as claimed in claim 11, wherein the two support elements are formed by a single bent wire.

14. A filter as claimed in claim 13, wherein the distal ends of the two support elements are coupled to the distal coupling part.

15. An embolic protection filter comprising:
a polymeric membrane having a proximal inlet end and a distal outlet end, the inlet end of the filter membrane having a single inlet hole sized to allow blood and embolic material enter the filter membrane, the outlet end of the filter membrane having a plurality of outlet openings sized to allow through passage of blood but to retain undesired embolic material within the filter membrane; and
a support frame to support the filter membrane in an expanded position, the support frame comprising two support elements which form a partial helical structure along the periphery of the filter membrane, each of the two support elements having a proximal end and a distal end, the two support elements defining a loop structure by joining the proximal ends of each of the two support elements and joining an intermediate point of each of the two support elements, the loop structure extending around and supporting the inlet hole of the filter membrane.

16. A filter as claimed in claim 15, wherein in the expanded position, the loop structure is in a plane that is transverse to the longitudinal axis of the filter, and the plane is tilted on an angle proximally to distally relative to a plane that is transverse and perpendicular to the longitudinal axis of the filter, such that one end of the loop structure is set back proximally of the opposing end of the loop structure.

17. A filter as claimed in claim 16, further comprising:
a proximal collar for coupling the filter to a guidewire, a proximal end of the support frame coupled to the collar via a flexible tether, the tether being movable independently of the support frame.

18. A filter as claimed in claim 17, further comprising:
a distal coupling part for directly coupling the support frame to a guidewire; wherein
the proximal collar is separate from and longitudinally spaced apart from the distal coupling part; and
the support frame couples the proximal collar to the distal coupling part.

19. A filter as claimed in claim 17, wherein the tether has a low column strength relative to the support elements.

20. A filter as claimed in claim 15, wherein the two support elements are formed by a single bent wire.

* * * * *